United States Patent
Oon et al.

(10) Patent No.: US 7,038,035 B1
(45) Date of Patent: May 2, 2006

(54) VACCINE-INDUCED HEPATITIS B VIRAL STRAIN AND USES THEREOF

(75) Inventors: Chong Jin Oon, Singapore (SG); Gek Keow Lim, Singapore (SG); Ai Lin Leong, Singapore (SG); Yi Zhao, Singapore (SG); Wei Ning Chen, Singapore (SG)

(73) Assignee: Government of Republic of Singapore, Singapore (SG)

( * ) Notice: Subject to any disclaimer, the term of this patent is extended or adjusted under 35 U.S.C. 154(b) by 0 days.

(21) Appl. No.: 09/719,533

(22) PCT Filed: Jun. 19, 1998

(86) PCT No.: PCT/SG98/00045

§ 371 (c)(1),
(2), (4) Date: Jul. 10, 2001

(87) PCT Pub. No.: WO99/66048

PCT Pub. Date: Dec. 23, 1999

(51) Int. Cl.
 *C07H 21/04* (2006.01)
 *C12N 7/00* (2006.01)
 *C12N 7/01* (2006.01)
 *C12N 15/09* (2006.01)
 *C12N 15/51* (2006.01)

(52) U.S. Cl. ............. 536/23.72; 536/23.1; 536/23.7; 435/69.1; 435/69.3; 435/235.1; 435/320.1; 424/184.1; 424/186.1; 424/189.1; 424/204.1; 424/227.1

(58) Field of Classification Search ............. 536/23.72, 536/23.7, 24.3; 435/320.1, 69.1, 69.2; 424/184.1, 424/185.1, 186.1, 189.1, 204.1, 227.1; 514/2, 514/44; 530/300, 350
See application file for complete search history.

(56) References Cited

U.S. PATENT DOCUMENTS 5,830,759 A * 11/1998 Chang et al. ............. 435/372.2

FOREIGN PATENT DOCUMENTS

| WO | WO91/14703 | * 10/1991 |
| WO | 9521189 | 8/1995 |
| WO | 9811916 | 3/1998 |

OTHER PUBLICATIONS

Oon et al., Molecular epidemiology of hepatitis B virus vaccine variants in Singapore. Vaccine 13 (8):699-702, 1995.*
Ho et al., Clinical and Diagnositic Laboratory Immunology, vol. 2 No 6, pp. 760-762 (Nov. 1995).*
Norder et al., Journal of General Viology, vol. 73, pp. 1201-1208 (1992).*
Norder et al., Journal of General Viology, vol. 74, pp. 1341-1348 (1993).*

VACCINE-INDUCED HEPATITIS B VIRAL STRAIN AND USES THEREOF

Throughout this application, various references are referred to within parentheses. Disclosures of these publications in their entireties are hereby incorporated by reference into this application to more fully describe the state of the art to which this invention pertains.

BACKGROUND OF THE INVENTION

The present invention concerns the hepatitis B virus genome with a vaccine-induced mutation at amino acid residue 145 (Glycine to Arginine) within the major surface antigen, its nucleotide sequence, the deduced four major protein sequences, antigen, antibody, detection systems, development of effective vaccines, and antiviral agents.

The hepatitis B virus was first discovered in 1963 as a human virus that is transmitted parenterally. Although these viruses are not particularly cytotoxic and do not lead to massive cell death, they have been the cause of a major infectious disease affecting both adults and young children worldwide. The presence of hepatitis B surface antigen has served as the main detection marker for carriers of hepatitis B virus, and thus, possibly those at risk of transmitting the virus. Conversely, the occurrence of an anti-surface antigen antibody indicates an immune response which would lead to eventual recovery. Stimulation of such immune response has been greatly helped by the currently licensed hepatitis B vaccines developed by Merck Sharpe & Dohme. These vaccines contain the major surface antigen in either the natural (plasma-derived) or the recombinant (purified from yeast cells) form, and have proven safe and effective in neutralizing the hepatitis B virus. In Singapore, the active vaccination program at a national scale has resulted in a significant decrease of acute hepatitis B infection and the incidence of primary hepatocellular carcinoma. This decrease has in turn been associated with an increased immunity in the population.

The major antigenic epitope of hepatitis B virus is a highly conserved region spanning 23 amino acid residues and located from amino acid position 124 to 147 of the major surface antigen. This small region designated as the group specific determinant "a" is found in all subtypes and isolates of hepatitis B viral genomes. Its antigenic properties seem due to its proposed double loop structure, to which the vaccine-induced neutralizing antibody binds.

In contrast to random mutations introduced into hepatitis B viral genomes during viral replication by the proof-reading defective reverse transcriptase, mutations induced following vaccination occur mainly in the "a" epitope of the major surface antigen. These mutant viruses are of particular interest since they show reduced affinity to the neutralizing antibody and therefore are able to replicate independently. Among these vaccine-escape mutants, the mutation at amino acid residue 145 (from Glycine to Arginine) in the second loop of the major surface antigen is the most significant because it is stable, results in conformational changes of the "a" epitope and has been reported worldwide in North America, Europe, Japan and Southeast Asia. In Singapore, for example, such mutants are the most frequent variant following vaccination. Twelve infectious variants among 41 breakthroughs have been identified as having an arginine mutation at amino acid residue 145 of the major surface antigen. There is evidence of vertical transmission from one of the 12 variants and this variant has also been associated with active liver disease. Significantly, some of these variants are now found in random asymptomatic adult population.

The occurrence of this replicative vaccine-induced mutant and its ability to escape detection using standard reagents is of grave concern because it has resulted in the development of acute hepatitis B in Italy and Singapore. This situation therefore requires the urgent development of specific detection systems, as well as, effective prophylactic vaccines and antiviral agents. Determination of the nucleotide sequence of this vaccine-induced mutant virus constitutes the first step towards these aims and will certainly be helpful for the various above-mentioned developments.

SUMMARY OF THE INVENTION

This invention provides an isolated strain of Hepatitis B virus designated Human Hepatitis B Virus Surface Antigen-'S'-145 Singapore Strain (Glycine to Arginine) which constituent viral genome is deposited under Accession Nos. P97121504, P97121505, and P97121506 on 15 Dec. 1997, at the European Collection of Cell Cultures (ECACC):

European Collection of Cell Cultures
Vaccine Research and Production Laboratory Public Health Laboratory Service
Centre for Applied Microbiology and Research
Porton Down
Salisbury, Wiltshire SP4 0JG
United Kingdom.

This invention also provides an isolated nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine rather than a glycine.

This invention provides a method of producing the polypeptide in purified form and the resulting purified polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine rather than a glycine.

This invention provides an oligonucleotide of at least 15 nucleotides capable of specifically hybridizing with sequences of only the mutant viral strain of hepatitis B virus.

This invention provides a method of obtaining antibodies to a polypeptide which is a mutant major surface antigen of a strain of hepatitis B virus and the antibodies produced.

This invention provides a method of obtaining antibodies to a polypeptide which is a mutant major surface antigen of a strain of hepatitis B virus and the antibodies produced. This invention provides a method of determining whether a subject is infected with the above-described viral strain.

This invention also provides a composition capable of stimulating or enhancing antibody production for the polypeptide.

This invention further provides a method for identifying a chemical compound which is capable of treating and/or preventing an infection by the above-described mutant viral strain and compositions containing such compounds.

This invention also provides a composition comprising the chemical compound identified by the above-described methods in an amount effective to treat or prevent infection by the strain and a pharmaceutically effective carrier.

This invention further provides use of compositions for treating a subject infected with this viral strain.

This invention also provides use of compositions for preventing infection of a subject by this viral strain.

And lastly, this invention provides a method of screening bodily fluids for this viral strain.

DETAILED DESCRIPTION

SEQ. ID NO: 1 is a whole nucleotide sequence of human hepatitis B virus, isolated from an eleven year old child born to a mother in Singapore with the wild type virus. The child had received standard Hepatitis B immunoglobulin (HBIG) and HB vaccine and was infected with the mutated strain one year later. This strain carries a mutation at amino acid residue 145 (glycine to arginine) of the major surface antigen (SEQ. I.D. No. 1). The mutation is shown at nucleic acids numbered 587–589.

SEQ ID NO:2 is the deduced amino acid sequence of the DNA polymerase from the nucleotide sequence of SEQ ID NO:1.

SEQ ID NO:3 is the deduced amino acid sequence of the large surface antigen from the nucleotide sequence of SEQ ID NO: 1. The mutated amino acid residue (G to R) is numbered 319.

SEQ ID NO:4 is the deduced amino acid sequence of the core protein from the nucleotide sequence of SEQ ID NO:1.

SEQ ID NO:5 is the deduced amino acid sequence of the trans-activating X protein from the nucleotide sequence of SEQ ID NO:1.

SEQ ID NO:6 is the oligonucleotide sequence corresponding to the initiation site of the coding region of DNA polymerase, at position 2307 of the viral genome and matches the coding strand (sense oligonucleotide).

SEQ ID NO:7 is the oligonucleotide sequence corresponding to position 250 of the viral nucleotide sequence and matches the complementary strand (anti-sense oligonucleotide).

SEQ ID NO:8 is the oligonucleotide sequence corresponding to position 250 of the viral nucleotide sequence and matches the coding strand (sense oligonucleotide).

SEQ ID NO:9 is the oligonucleotide sequence corresponding to the stop codon of the coding region of DNA polymerase, at position 1623 of the viral genome and matches the complementary strand (anti-sense oligonucleotide).

SEQ ID NO:10 is the oligonucleotide sequence corresponding to position 1420 of the viral genome and matches the coding strand (sense oligonucleotide).

SEQ ID NO:11 is the oligonucleotide sequence corresponding to position 2340 of the viral genome and matches the complementary strand (anti-sense oligonucleotide).

DETAILED DESCRIPTION OF THE INVENTION

Throughout this application, references to specific nucleotides are to nucleotides present on the coding strand of the nucleic acid. The following standard abbreviations are used throughout the specification to indicate specific nucleotides:

C=cytosine A=adenosine

T=thymidine G=guanosine

The present invention provides the nucleotide sequence of a hepatitis B virus genome, which carries a vaccine-induced mutation at amino acid residue 145 (Glycine to Arginine) of the major surface antigen, consisting of 3215 nucleotides (SEQ ID NO: 1) coding for 4 overlapping viral proteins.

The invention provides amino acid sequences of the four major viral proteins, these include the DNA polymerase, large/middle/major surface antigen, core and trans-activating X. These proteins can be produced using recombinant technology, and used in developing polyclonal or monoclonal antibodies.

The present invention also provides a hepatitis B virus diagnostic system, specific for the vaccine-induced mutation at amino acid residue 145 (Glycine to Arginine) of the major surface antigen, using nucleotide or protein sequences or antibodies described herein.

The present invention provides an isolated strain of Hepatitis B virus designated Human Hepatitis B Virus Surface Antigen-'S'-145 Singapore Strain (Glycine to Arginine) which constituent viral genome is deposited under Accession Nos. P97121504, P97121505 and P97121506.

The invention also provides an isolated nucleic acid encoding a polypeptide which is a mutant major surface antigen of a strain of hepatitis B virus, such polypeptide having an amino acid sequence which differs from the amino acid sequence of the major surface antigen of a wild type hepatitis B virus in that the amino acid at position number 145 of such polypeptide is an arginine rather than a glycine. In a specific embodiment, the polypeptide is being encoded by nucleotides 155 through 835 of the nucleic acid sequence designated SEQ. I.D. No. 1, specifically, comprising nucleotides "AGA" in position 587–589, instead of "GGA." This nucleic acid can be DNA or RNA, specifically, cDNA or genomic DNA.

In another embodiment of the invention, the polypeptide has an amino acid sequence substantially the same as amino acid residues 174 through 400 of the amino acid sequence designated SEQ. I.D. No. 3.

This invention further provides an isolated nucleic acid which encodes a peptide, wherein the peptide is encoded by a nucleic acid molecule comprising nucleotides 527 through 595 of SEQ. I.D. No. 1.

This Invention also provides an isolated nucleic acid which encodes a peptide, wherein the peptide has an amino acid sequence comprising amino acid residues 298 through 320 of the amino acid sequence designated SEQ. I.D. No. 3.

This invention also provides a vector comprising an isolated nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine rather than a glycine and operatively linked to a promoter of RNA transcription.

Further, this invention provides a vector comprising an isolated nucleic acid encoding a peptide, wherein the peptide is encoded by a nucleic acid molecule comprising nucleotides 527 through 595 of SEQ. I.D. No. 1.

In both of the above-identified vectors, the vector may comprise viral DNA.

This invention also provides a host vector system for the production of a polypeptide which comprises the above-described vectors in a suitable host.

This invention also provides a method of producing a polypeptide or a peptide which comprises growing the host vector systems described above, under suitable conditions permitting production of the polypeptide and recovering the polypeptide so produced.

This invention further provides a method of obtaining a polypeptide or a peptide in purified form which comprises: (a) introducing the above-described vectors into a suitable host cell; (b) culturing the resulting host cell so as to produce the polypeptide; (c) recovering the polypeptide produced in step (b); and (d) purifying the polypeptide so recovered.

This invention further provides a purified polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine rather than a glycine. One means of obtaining the polypeptide is by the above-described method.

This invention also provides a purified peptide, wherein the peptide has an amino acid sequence comprising amino acid residues 298 through 320 of the amino acid sequence designated Seq. I.D. No. 3. One means of obtaining this peptide is by the above-describe method.

This invention also provides an oligonucleotide of at least 15 nucleotides capable of specifically hybridizing with a unique sequence of nucleotides within a nucleic acid which encodes a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine rather than a glycine, without hybridizing to any sequence of nucleotides within a nucleic acid which encodes the major surface antigen of a wild type hepatitis B virus. Specifically the oligonucleotide comprises nucleotides 527 through 595 of SEQ. I.D. No. 1.

This invention also provides a method of obtaining antibodies to a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine, and not to the major surface antigen of a wild type hepatitis B virus, comprising: (a) obtaining the polypeptide in a purified form; (b) immunizing an organism capable of producing antibodies against the purified polypeptide; (c) collecting the produced antibodies; (d) combining the produced antibodies and the purified polypeptide under conditions to form a complex; and (e) determining which produced antibodies form a complex with the purified polypeptide so as to obtain antibodies to the polypeptide. Specifically, the polypeptide is being encoded by nucleotides 155 through 835 of the nucleic acid sequence designated SEQ. I.D. No. 1. In another embodiment, the polypeptide has an amino acid sequence substantially identical to amino acid residues 174 through 400 of the amino acid sequence designated SEQ. I.D. No. 3.

One could perform the above-described well-known method in rabbits or mice.

This invention also provides a method of obtaining antibodies to a peptide, wherein the peptide has an amino acid sequence comprising amino acid residues 298 through 320 of the amino acid sequence designated SEQ. I.D. No. 3, comprising: (a) obtaining the peptide in a purified form; (b) immunizing an organism capable of producing antibodies against the purified peptide; (c) collecting the produced antibodies; (d) combining the produced antibodies and the purified peptide under conditions to form a complex; and (e) determining which produced antibodies form a complex with the purified peptide so as to obtain antibodies to the peptide.

One could perform the above-described well-known method in rabbits or mice.

This invention also provides the antibodies obtained from the above-described methods, specifically the monoclonal antibodies. Further, the invention provides antibodies capable of detecting a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine, and incapable of detecting the major surface antigen of a wild type hepatitis B virus, as well as, antibodies capable of detecting a peptide, wherein the peptide has an amino acid sequence comprising amino acid residues 298 through 320 of the amino acid sequence designated SEQ. I.D. No. 3.

This invention also provides use of an isolated nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine for determining whether a subject is infected with a strain of Hepatitis B virus designated Human Hepatitis B Virus Surface Antigen-'S'-145 Singapore Strain (Glycine to Arginine), wherein such determination comprises: (a) obtaining an appropriate nucleic acid sample from the subject; and (b) determining whether the nucleic acid sample from step (a) is, or is derived from, a nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine.

A means of determination is where the nucleic acid sample in step (a) comprises mRNA corresponding to the transcript of DNA encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine, and wherein the determining of step b) comprises: (i) contacting the mRNA with the above-described oligonucleotide under conditions permitting binding of the mRNA to the oligonucleotide so as to form a complex; (ii) isolating the complex so formed; and (iii) identifying the mRNA in the isolated complex so as to thereby determine whether the mRNA is, or is derived from, a nucleic acid which encodes the polypeptide.

Another example is where the nucleic acid sample in step (a) comprises mRNA corresponding to the transcript of DNA encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine, and wherein the determining of step (b) comprises: (i) translating the mRNA under suitable conditions to obtain an amino acid sequence; and (ii) comparing the amino acid sequence of step (i) which the amino acid sequence of an isolated nucleic acid which encodes a polypeptide, wherein the polypeptide has an amino acid sequence substantially identical to amino acid residues 174 through 400 of the amino acid sequence designated SEQ. I.D. No. 3 so as to thereby determine whether the nucleic acid sample is, or is derived from, a cucleic acid which encodes the polypeptide. A further example is where the determining of step (b) comprises: (i) amplifying the nucleic acid present in the sample of step (a); and (ii) detecting the presence of polypeptide in the resulting amplified nucleic acid.

This invention provides the use of an antibody that recognizes a polypeptide which is a mutant major surface antigen of a train of hepatitis B virus for determining whether the subject has a predisposition for hepatocellular carcinoma, wherein such determination comprises: (a) obtaining an appropriate nucleic acid sample from the subject; and (b) determining whether the nucleic acid sample from step (a) is, or is derived from, a nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine, by contacting the sample under appropriate conditions to bind to the antibodies of claim 35 so as to determine whether the subject has a predisposition for hepatocellular carcinoma.

The invention also provides use of antibodies capable of detecting a polypeptide which is a mutant major surface antigen of a strain of Hepatitis B virus designated Human Hepatitis B Virus Surface Antigen-'S'-145 Singapore Strain (Glycine to Arginine) for determining whether a subject is infected with a strain of Hepatitis B virus designated Human Hepatitis B Virus Surface Antigen-'S'-145 Singapore Strain (Glycine to Arginine), wherein such determination comprises: (a) obtaining an appropriate sample from the subject; and (b) determining whether the sample from step (a) is, or is derived from, a nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine by contacting the sample under appropriate conditions to bind to the antibodies so as to determine whether a subject is infected. Furthermore, the antibody may also be capable detecting a peptide, wherein the peptide has an amino acid sequence comprising amino acid residues 298–320 of the amino acid sequence designated SEQ. I.D. No. 3.

In the above-described uses, the isolated nucleic acid, oligonucleotide or antibody may be labeled with a detectable marker. Examples of detectable markers include radioactive isotopes, fluorophors and enzymes.

In a specific embodiment, the sample includes, but is not limited to, blood, tissue or sera.

This invention also provides a method for identifying a chemical compound for the manufacture of a medicament which is capable of treating infection by a strain of Hepatitis B virus designated Human Hepatitis B Virus Surface Antigen-'S'-145 Singapore Strain (Glycine to Arginine) which comprises: (a) contacting a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine, with the chemical compound under conditions permitting binding between the polypeptide and the chemical compound; (b) detecting specific binding of the chemical compound to the polypeptide; and (c) determining whether the chemical compound inhibits the polypeptide so as to identify a chemical compound which is capable of treating infection by the viral strain.

This invention also provides a method for identifying a chemical compound for the manufacture of a medicament which is capable of preventing infection by a strain of Hepatitis B virus designated Human Hepatitis B Virus Surface Antigen-'S'-145 Singapore Strain (Glycine to Arginine), which comprises: (a) contacting a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine, with the chemical compound under conditions permitting binding between the polypeptide and the chemical compound; (b) detecting specific binding of the chemical compound to the polypeptide; and (c) determining whether the chemical compound inhibits the polypeptide so as to identify a chemical compound which is capable of preventing infection by the viral strain.

This invention further provides a composition comprising a polypeptide which is a mutant major surface antigen of a strain of hepatitis B virus, such polypeptide having an amino acid sequence which differs from the amino acid sequence of a major surface antigen of a wild type hepatitis B virus in that the amino acid at posit on number 145 of such polypeptide is an arginine, rather than a glycine, or derivative thereof, the amounts of such polypeptide being effective to stimulate or enhance antibody production in a subject, and a pharmaceutically acceptable carrier.

The actual effective amount will be based upon the size of the polypeptide, the biodegradability of the polypeptide, the bioactivity of the polypeptide and the bioavailability of the polypeptide. If the polypeptide does not degrade quickly, is bioavailable and highly active, a smaller amount will be required to be effective. The effective amount will be known to one of skill in the art; it will also be dependent upon the form of the polypeptide, the size of the polypeptide and the bioactivity of the polypeptide. Use of an adjuvant for example, would lower the required amount of the polypeptide. One of skill in the art could routinely perform empirical activity tests to determine the bioactivity in bioassays and thus determine the effective amount.

Pharmaceutically acceptable carriers are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention further provides a composition comprising a peptide, wherein the peptide has an amino acid sequence comprising amino acid residues 298 through 320 of the amino acid sequence designated SEQ. I.D. No. 3 or derivative thereof, the amounts of such peptide being effective to stimulate or enhance antibody production in a subject, and a pharmaceutically acceptable carrier.

This invention further provides compositions comprising the chemical compound identified by the above-described methods in an amount effective to treat or prevent infection by a strain of Hepatitis B virus designated Human Hepatitis B Virus Surface Antigen-'S'-145 Singapore Strain (Glycine to Arginine) and a pharmaceutically effective carrier.

This invention provides the use of the above-described compositions as medicaments for treating and/or preventing hepatocellular carcinoma.

This invention also provides use of the above-identified compositions for treating a subject infected with a strain of Hepatitis B virus designated Human Hepatitis B Virus Surface Antigen-'S'-145 Singapore Strain (Glycine to Arginine).

This invention also provides use of the above-identified compositions for preventing infection by a strain of Hepatitis B virus designated Human Hepatitis B Virus Surface Antigen-'S'-145 Singapore Strain (Glycine to Arginine) in a subject which comprises administering an effective amount.

This invention further provides a method of screening tissues and bodily fluids from a subject for a strain of hepatitis B virus designated Human Hepatitis B Virus Surface Antigen-'S'-145 Singapore Strain (Glycine to Arginine) which comprises: (a) obtaining an appropriate sample of bodily fluid from the subject; (b) determining the presence of a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine in the sample of step (a) so as to screen the sample for the strain. In embodiments of this method, the bodily fluid comprises blood, sera, or a nucleic acid sample of blood or sera.

This invention provides a method for determining whether a subject has a predisposition for hepatocellular carcinoma, which comprises: (a) obtaining an appropriate nucleic acid sample from the subject; and (b) determining whether the nucleic acid sample from step (a) is, or is derived from, a nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine, thereby determining whether the subject has a predisposition for hepatocellular carcinoma.

This invention also provides the above-described method, wherein the nucleic acid sample in step (a) comprises mRNA encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine, and wherein the determining of step (b) comprises: (i) contacting the mRNA with the above-described oligonucleotides under conditions permitting binding of the mRNA to the oligonucleotide so as to form a complex; (ii) isolating the complex so formed; and (iii) identifying the mRNA in the isolated complex so as to thereby determine whether the mRNA is, or is derived from, a nucleic acid which encodes the polypeptide.

This invention further provides the above-described method, wherein the nucleic acid sample in step (a) comprises mRNA encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine, and wherein the determining of step (b) comprises: (i) translating the mRNA under suitable conditions to obtain an amino acid sequence; and (ii) comparing the amino acid sequence of step (i) with the amino acid sequence encoded by the isolated nucleic acid described above so as to determine whether the nucleic acid sample is, or is derived from, a nucleic acid which encodes the polypeptide.

This invention also provides the above-described method, wherein the determining of step (b) comprises: (i) amplifying the nucleic acid present in the sample of step (a); and (ii) detecting the presence of polypeptide in the resulting amplified nucleic acid.

This invention further provides the above-described method for determining whether a subject has a predisposition for hepatocellular carcinoma, which comprises: (a) obtaining an appropriate sample from the subject; and (b) determining whether the sample from step (a) is, or is derived from, a nucleic acid encoding a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine, by contacting the sample under appropriate conditions to bind to the above-described antibodies so as to determine whether the subject has a predisposition for hepatocellular carcinoma.

This invention provides the above-described methods, wherein the oligonucleotide or antibody is labeled with a detectable marker.

This invention also provides the above-described methods, wherein the detectable marker is a radioactive isotope, a fluorophor or an enzyme.

This invention also provides the above-described methods, wherein the sample comprises blood, tissue or sera.

This invention further provides a method for identifying a chemical compound for the manufacture of a medicament which is capable of treating hepatocellular carcinoma which comprises: (a) contacting a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine, with the chemical compound under conditions permitting binding between the polypeptide and the chemical compound; (b) detecting specific binding of the chemical compound to the polypeptide; and (c) determining whether the chemical compound binds to the polypeptide so as to identify a chemical compound which is capable of treating hepatocellular carcinoma.

This invention provides a method for identifying a chemical compound for the manufacture of a medicament which is capable of preventing hepatocellular carcinoma, which comprises: (a) contacting a polypeptide which is a mutant major surface antigen of a strain of hepatitis B virus, such polypeptide having an amino acid sequence which differs from the amino acid sequence of a major surface antigen of a wild type hepatitis B virus in that the amino acid at position number 145 of such polypeptide is an arginine, rather than a glycine, with the chemical compound under conditions permitting binding between the polypeptide and the chemical compound; (b) detecting specific binding of the chemical compound to the polypeptide; and (c) determining whether the chemical compound binds to the polypeptide so as to identify a chemical compound which is capable of preventing hepatocellular carcinoma.

Additionally, this invention provides a composition comprising the chemical compound identified by the above-described methods in an amount effective to treat hepatocellular carcinoma and a pharmaceutically effective carrier.

This invention also provides a composition comprising the chemical compound identified by the above-described methods in an amount effective to prevent hepatocellular carcinoma and a pharmaceutically effective carrier.

This invention further provides a method treating a subject with hepatocellular carcinoma which comprises administering an effective amount of the above-described compositions.

This invention further provides a method preventing hepatocellular carcinoma in a subject which comprises administering an effective amount of the above-described compositions.

This invention also provides a hepatitis vaccine, comprising a mutant form of the surface antigen of hepatitis B virus, such polypeptide having an amino acid sequence which differs from the amino acid sequence of the major surface antigen of hepatitis B in that the amino acid at position number 145 of such polypeptide is an arginine rather than a glycine.

This invention also provides the above-described vaccine and an adjuvant.

This invention is Illustrated in the Experimental Details section which follows. These sections are set forth to aid in an understanding of the invention but are not intended to, and should not be construed to, limit in any way the invention as set forth in the claims which follow thereafter.

Experimental Details

In the method described below, the hepatitis B virus carrying the mutation at amino acid residue 145 of the major surface antigen was isolated, and its nucleotide sequence was determined.

Serum sample (20/815c) was obtained from an 11-year old child born to a mother carrying the wild type surface antigen. The child tested surface antigen negative at birth and was subjected to a combined treatment of hepatitis B immunoglobulin (HBIG) and plasma-derived vaccine. He was tested surface antigen positive one year later and carried an Arginine mutation at amino acid residue 145 in the major surface antigen. The viral DNA was extracted prior to the determination of its sequence in the present invention.

As described in the Examples below, the genome of this hepatitis B mutant virus carrying a mutation at amino acid residue 145 of the major surface antigen consists of 3215 nucleotides which are identical to those of the wild type virus of the same subtype (adw). Open reading frames (ORFs) coding for the major viral proteins are found at corresponding positions when compared to the wild type virus. Position 1 in the mutant hepatitis B virus genome is defined according to that in the wild type virus, corresponding to the restriction site EcoRI which is absent in the hepatitis B virus in the present invention due to changes in the nucleotide sequence.

Figure 1:
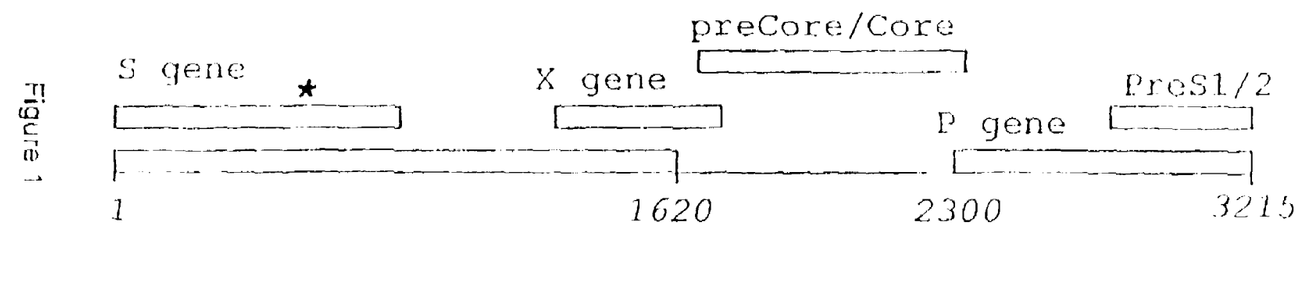
FIG. 1. Structure of the four open reading frames of human hepatitis B viral genome isolated from a male, e even year old Singaporean child with a glycine to arginine mutation at amino acid residue 145 of the major surface antigen, as labeled by an asterisk. The major viral proteins: DNA polymerase, large/middle/major surface antigen, precore, core and transactivating X are denoted as P, PreS 1/PreS2/S, PreC, C and X respectively.

The structure of the different ORFs in the mutant virus genome reported are summarized in FIG. 1 and their locations are indicated as follows:

DNA polymerase gene starts at position 2307 and ends at position 1623, therefore consisting of 2532 nucleotides and coding for 843 amino acid residues;

Large surface antigen gene starts at position 2848 and ends at position 835, therefore consisting of 1203 nucleotides and coding for 400 amino acid residues. This large surface antigen over laps the middle surface antigen starting at position 3205 and the major surface antigen which starts at position 155. Both the middle (consisting of 231 amino acids residues) and the major (consisting of 226 amino acid residues) surface antigens end at the same position as the large surface antigen;

Core gene starts at position 1814 and ends at position 2452, therefore consisting of 639 nucleotides and coding for 212 amino acid residues; and Trans-activating X gene starts at position 1374 and ends at position 1838, therefore consisting of 465 nucleotides and coding for 154 amino acid residues.

Furthermore, sequence analysis has established this mutant hepatitis B virus as belonging to adw subtype, as indicated by a lysine residue at both positions 122 and 160 in the major surface antigen. Consistent with previous analysis of the "a" epitope by direct sequencing, the vaccine-induced mutation (from Glycine to Arginine) is found at amino acid residue 145 of the major surface antigen.

Compared with the wild type hepatitis B virus deposited in the Genbank database (accession number D00329), the identity of this hepatitis B viral strain is at 89.4% for the nucleotide sequence. The identity of different viral proteins of the present mutant hepatitis B virus as compared with its wild type counterparts is at 88.3%, 87.7%, 93.4% and 87% for DNA polymerase (PIR—Protein Identification Resources accession number P93460), large surface antigen (PIR accession number A93460), core (PIR accession number C93460) and trans-activating X (PIR accession number A31289) proteins, respectively.

The hepatitis B virus genome in the present invention carrying a vaccine-induced mutation at amino acid residue 145 (Glycine to Arginine) of the major surface antigen, can be used as material to design oligonucleotides specific to the mutant virus genome. These oligonucleotides can be used as material for highly specific diagnostic agents that detect virus carrying a vaccine-induced mutation at amino acid residue 145 of the major surface antigen.

The hepatitis B virus genome in the present invention, with a vaccine-induced mutation at amino acid residue 145 (Glycine to Arginine) of the major surface antigen, can be used as material to produce proteins of the invention by expressing a vector that carries the relevant coding region, and which can replicate in a host cell such as *Escherichia coli*, by standard DNA recombinant technology.

Proteins of the present invention are useful as material for highly specific diagnostic agents capable of detecting hepatitis B virus carrying a vaccine-induced mutation at amino acid residue 145 of the major surface antigen. Using known methods, these same proteins can be used to produce polyclonal and monoclonal antibodies.

Polyclonal and monoclonal antibodies can be used as material for diagnostic agents to detect with high specificity antigens of hepatitis B virus, with a vaccine-induced mutation at amino acid residue 145 (Glycine to Arginine) of the major surface antigen.

A detection system using each protein of the present invention or proteins with partial replacement of amino acids, and a detection system using monoclonal or polyclonal antibodies to such proteins, are useful as highly specific diagnostic agents or hepatitis B virus with vaccine-induced mutation at amino acid residue 145 of the major surface antigen, and are effective to detect and screen out such virus from transfusion bloods or blood derivatives. The proteins or antibodies to such proteins, can be used as a material for development of prophylactic and therapeutic vaccine against such virus.

It is well known that one or more nucleotides in a DNA sequence can, be substituted by other nucleotides to produce the same protein. The present invention also concerns such nucleotide changes which code for proteins reported in this invention. It is equally well known that one or more amino acids in a protein sequence can be replaced by other analogous amino acids, as defined by their hydrophilic properties or charges, to produce an analog of the amino acid sequence. Any analogs of the proteins of the present invention involving amino acid replacement, deletions, or by isosteres (modified amino acids that bear close structural and spatial similarity to protein amino acids), amino acid addition, or isostere addition can be utilized, provided that the resulting sequences elicit antibodies recognizing hepatitis B virus with a vaccine-induced mutation at amino acid mutation 145 (Glycine to Arginine) of the major surface antigen.

EXAMPLES

The nucleotide sequence and the deduced amino acid sequence of hepatitis B virus, carrying a vaccine-induced mutation at amino acid residue 145 (Glycine to Arginine) of the major surface antigen, were determined in the following manner:

1. Isolation of Viral DNA

The viral DNA was isolated from a serum sample (20/815c) obtained from the serum of an 11-year old Chinese child who was born to a mother of wild type hepatitis B virus surface antigen. Despite negative test results at birth, he was given combined treatment of HBIG and the plasma-derived vaccine and tested positive for hepatitis B virus surface antigen one year later. Sequence analysis of the "a" epitope indicated the presence of a vaccine-induced mutation at amino acid residue 145 of the major surface antigen.

The Isolation Method Used was:

200 μl of the serum sample was added with 400 μl of the lysis buffer (Tris chloride 10 mM, pH7.4, EDTA 1 mM, and sodium dodecyl sulfate 2%) and 25 μl of proteinase K (20 mg/ml) incubated at 65 C for 3 hours. Viral DNA was then extracted by phenol/chloroform and precipitated by ethanol.

2. Amplification of Viral DNA by Polymerase Chain Reaction (PCR)

Figure 2:
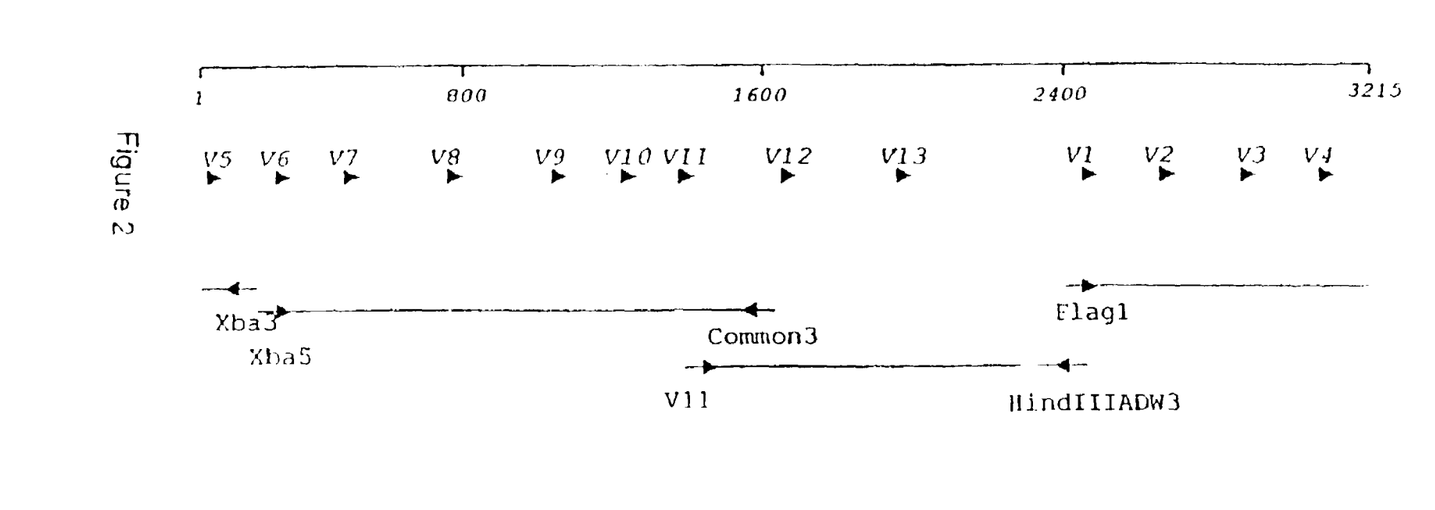
FIG. 2. A map showing positions of oligonucleotide V1 to V13 for use in the sequence determination of the hepatitis B viral genome that is shown in FIG. 1.

The virus genome was amplified by polymerase chain reaction (PCR) using 3 sets of overlapping oligonucleotides, which were designed according to the wild type hepatitis B virus of adw subtype. Various restriction enzyme sites were included to facilitate the cloning of the PCR products. The position of these oligonucleotides is shown in FIG. 2 and indicated as follows:

Flag 1 (ATAAGCTTATCCCCCTATCTTATCAA-CACTTCCGGA) (SEQ. I.D. No. 6) starts at the initiation site of the coding region of DNA polymerase, at position 2307 of the viral nucleotide sequence and matches the coding strand (sense oligonucleotide). An additional HindIII restriction enzyme site is underlined;

Xba3 (GAGTCTAGACTCTGCGGTATTGTGA) (SEQ. I.D. No. 7) starts at the internal restriction enzyme site XbaI, at position 250 of the viral nucleotide sequence and matches the complementary strand (anti-sense oligonucleotide). An additional XbaI restriction enzyme site is underlined;

Xba5 (GAGTCTAGACTCGTGGTGGACTTCT) (SEQ. I.D. No. 8) starts at the internal XbaI site, at the same location as that of Xba3 oligonucleotide but matches the coding strand (sense oligonucleotide). An additional XbaI restriction enzyme site is underlined;

Common 3 (TGAGAATTCTCACGGTGGTCTCCAT-GCGACGT) (SEQ. I.D. No. 9) starts at the stop codon of the DNA polymerase, at position 1623 of the viral nucleotide sequence and matches the complementary strand (anti-sense oligonucleotide). An additional EcoRI restriction enzyme site is underlined;

V11 (TTTGTTTACGTCCCGT) (SEQ. I.D. No. 10) starts near the initiation site of the X gene, at position 1420 of the viral nucleotide sequence and matches the coding strand (sense oligonucleotide);

HindIIIADW3 (CTAAGCTTAGTTTCCGGAAGTGT-TGAT) (SEQ. I.D. No. 11) starts close to the initiation site of the DNA polymerase, at position 2340 and matches the complementary strand (anti-sense oligonucleotide). An additional Hind III restriction enzyme site is underlined.

Using viral DNA as a template, PCR was then carried out on a DNA Thermal Cycler (Perkin-Elmer. Cetus) for 35 cycles using Pfu polymerase (Stratagene, U.S.A.), each cycle consisting of 1.5 minutes at a denaturing temperature of 94° C., 2 minutes at an annealing temperature of 53° C. and 4 minutes at an extension temperature of 72° C. The following combinations of oligonucleotides were used: Flag1/Xba3, Xba5/Common3 and V11/HindIIIADW3, and generating amplification products of 1.2 kb, 1.4 kb and 1.1 kb, respectively.

3. Cloning of the Amplified Viral DNA Fragments.

Amplified viral DNA fragment from Flag1/Xba3 (1.2 kb) was subjected to restriction enzyme digestion by HindIII and XbaI prior to cloning in a BlueScript plasmid pre-treated by the same restriction enzymes. Similar digestion with XbaI and EcoRI was applied to PCR product from Xba5/Common3 (1.4 kb) prior to cloning in a BlueScript plasmid pre-treated by XbaI and EcoRI. On the other hand, the DNA fragment amplified with V11 and HindIIIADW3 (1.1 kb) was directly cloned into ZeroBlunt plasmid, developed by Invitrogen (U.S.A.) for cloning blunt-end DNA fragments.

4. Determination of Nucleotide Sequence

Nucleotide sequence of the vaccine-induced hepatitis B virus in the present invention was determined on plasmid DNA template by chain-terminating inhibitors, using the Sequenase DNA Sequencing Kit (United States Biochemical Corp.). To facilitate the sequencing procedure, various internal oligonucleotides were designed (from V1 to V13) according to the wild type hepatitis B virus, and their positions are indicated in FIG. 2.

From the analysis described above, the full-length nucleotide sequence of the hepatitis B virus carrying a vaccine-induced mutation at amino acid residue 145 (Glycine to Arginine) of the major surface antigen was determined as shown in SEQ ID NO:1.

The deduced amino acid sequences coding for the major viral proteins are shown in FIGS. 4–7: hepatitis B viral DNA polymerase (SEQ ID NO:2), the large surface antigen (SEQ ID NO:3), the core protein (SEQ ID NO:4) and the trans-activating X protein (SEQ ID NO:5).

Alignment of the virus sequence in the present invention with other hepatitis B viral sequences, available in the Genbank database, will point to specific sequence differences which in turn can be used to design DNA probes. A detection system using polymerase chain reaction (PCR) can then be developed. Such PCR reactions will involve combinations of oligonucleotides specific to hepatitis B virus with a vaccine-induced mutation at the amino acid residue 145 (Glycine to Arginine) of the major surface antigen, thereby allowing highly specific detection of these mutant viral DNAs. Briefly, viral DNA can be extracted as described in this invention. PCR reactions can be performed using specific oligonucleotides using similar cycling conditions described above. Results can then be analyzed after resolving PCR products on a 1% agarose gel.

According to known immunological procedures, it is possible to determine epitopes from protein sequences such as those in FIGS. 4–7. Determination of these epitopes specific to hepatitis B virus with vaccine-induced mutation at amino acid residue 145 of the major surface antigen will allow the synthesis of peptides using genetic engineering methods, synthesis of the proteins, production of the antibodies, development of specific diagnostic reagents, development of prophylactic and therapeutic vaccines, and antiviral agents.

A detection system for antibodies against hepatitis B virus, with a vaccine-induced mutation at amino acid residue 145 of the major surface antigen, can be developed using polyvinyl microtiter plates and the sandwich method. Briefly, 50 µl of 5 µg/ml concentration of a hepatitis B virus (vaccine-induced mutant) peptide can be dispensed in each well of the microtiter plates and incubated overnight at room temperature for consolidation. Similar procedures can be applied to 's' protein purified from host cells such as *Escherichia coli*. The microplate wells can be washed five times with physiological saline solution containing 0.05% Tween 20. For overcoating, 100 µl of NaCl buffer containing 30% (v/v) of calf serum and 0.05% Tween 20 (CS buffer) can be dispensed in each well and discarded after incubation for 30 minutes at room temperature.

To determine antibodies specific for the vaccine-induced mutant hepatitis B virus antibodies in serum, the primary reaction can be carried out such that 50 µl of the CS buffer and 10 µl of a serum sample can be dispensed in each microplate well and incubated on a microplate vibrator for one hour at room temperature. After completion of the primary reaction, microplate wells are washed five times as described above.

In the secondary reaction, 1 ng of horseradish peroxidase labeled anti-human IgG mouse monoclonal antibodies dissolved in 50 µl of calf serum can be dispensed in each microplate well, and incubated on a microplate vibrator for one hour at room temperature. Upon completion, wells can be washed five times in the same way. After addition of hydrogen peroxide (as substrate) and 50 µl of O-phenylenediamine solution (as color developer) in each well, and after incubation for 30 minutes at room temperature, 50 µl of 4M sulphuric acid solution can be dispensed in each well to stop further color development and for reading absorbance at 490 nm.

The present invention makes possible detection of vaccine-induced mutant hepatitis B virus, in particular those carrying a mutation at amino acid residue 145 of the major surface antigen. Such mutant hepatitis B virus have hitherto escaped the detection using conventional antibody-based methods, and the present invention also provides detection systems capable of highly specific and sensitive detection at an early stage of infection.

In addition, these features allow accurate diagnosis of patients at an early stage of the disease and also help to remove with higher efficiency blood contaminated with vaccine-induced mutant hepatitis B virus through using a screening test of donor bloods.

Proteins and their antibodies under the present invention can be utilized for development of prophylactic and therapeutic vaccines, as well as, immunological pharmaceuticals. Sequence information on structural genes of these mutant viruses will be helpful in developing detection systems of the relevant protein antigens and antibodies.

Antigen-antibody complexes can be detected by known methods. Specific monoclonal and polyclonal antibodies can be raised by immunizing animals such as mice and rabbits with peptides or proteins specific to mutant vaccine-induced hepatitis B viruses. Inhibitory antiviral agents can be designed and targeted against these proteins and molecules in cell culture or in vivo.

The present invention is based on studies on an isolated virus genome with a vaccine-induced mutation at amino acid residue 145 (Glycine to Arginine) of the major surface antigen. The invention makes possible highly specific detection of these vaccine-induced mutant hepatitis B virus and provides materials such as protein, polyclonal and monoclonal antibodies for development of such detection system.

We have evidence showing that when expressed in a mammalian expression system, the major surface antigen (HBsAg) of the mutant HBV reported in our invention is detected as a 22 kDa protein on a Coomassie-blue stained SDS-PAGE gel, whereas the wild type HBsAg is detected as a 25 kDa protein. Since the only glycosylation site on the HBsAg is located in close proximity (Asparagine at position 146) to the mutation at position 145, it is very likely that the drastic change from Glycine to Arginine at position 145 affects the glycosylation process in the mutant HBsAg. This defective glycosylation process would in turn result in the smaller protein as observed in our studies. As the antigenicity of a protein is adversely affected by the extent of its glycosylation, we predict that the mutant HBsAg reported in our invention is more antigenic than the wild type HBsAg. This prediction is further supported by the structural analysis using the method developed by Hopp and Woods.

Our serological studies also indicate major differences between wild type HBV carriers and those carrying the mutant HBV reported in our invention, one such difference is that the serum viral DNA load is significantly lower at around 5 pg per ml as measured by an $^{125}$I hybridization assay (Abbott Laboratories, U.S.A.). In marked contrast, the wild type HBV DNA load is much higher at over 100 pg per ml. In addition, the anti-Hepatitis B surface antigen (anti-HBs) level is detectable at 10 IU per ml in the mutant HBV reported in our invention, whereas such antibodies remained undetectable in carriers of wild type HBV.

In the process of sequence determination, we have observed that a few oligonucleotides (each of them longer than 17 bases) designed according to the wild type HBV sequence, failed to hybridize to the mutant viral DNA reported in our invention. Two such oligonucleotides are located in the genome at positions 2711 to 2729 and 2902 to 2920. Our results, therefore, point to the structural differences between the wild type and mutant HBV genomes.

REFERENCES

1. Oon, C-J., "Viral hepatitis B in Singapore: epidemiology, prevention and control-monitoring the hepatitis B programme and management of carriers" *J. Royal College Physic. London* (1997) in press.
2. Oon, C-J., "Issues associated with HBV mutant strains" *J. Royal College Physic. London* (1997), in press.
   3. Oon, C-J., et al. "Hepatitis B surface antigen (HBsAg) mutants—their significance" *Annals Acad. Med. Singapore* (1997) in press.
   4. Oon, C-J., "Molecular epidemiology of hepatitis B 'a' variants and mutants: significance in immune population" *JAMA* (1996) 12: 5–6.
5. Goh, K-T, "Hepatitis B immunization in Singapore" *Lancet* (1996) 348: 1385–1386.
6. Oon, C-J., et al., "Natural history of hepatitis B surface antigen mutants in children" *Lancet* (1996) 348: 1524–1525.
7. Harrison, T. J., "Genetic variation in hepatitis B virus", *Eur. J. Gastroenter. & Hepatol.* (1996) 8: 306–311.
8. Oon, C-J., et al., "Molecular epidemiology of hepatitis B virus vaccine variants in Singapore" *Vaccine* (1995) 13: 699–702.
9. Carman, W., et al., "Viral genetic variation: hepatitis B virus as a-clinical example" *Lancet* (1993) 341: 349–353.
10. Harrison, T. J., "Variants of hepatitis B virus" *Vox Sang* (1992) 63: 161–167.
11. Harrison, T. J. et al., "Independent emergence of a vaccine-induced escape mutant of hepatitis B virus", *J. Hepatol.* (1991) 13: S105–107.
12. Carman, W. F. et al., "Vaccine-induced escape mutant of hepatitis B virus" *Lancet* (1990) 336: 325–329.

---

What is claimed is:

1. An isolated strain of Hepatitis B virus designated Human Hepatitis B Virus Surface Antigen-'S'-145 Singapore Strain (Glycine to Arginine) and deposited under any one of Accession Nos. P97121504, P97121505, or P97121506 with the European Collection of Cell Culture on 15$^{th}$ Dec. 1997.

2. An isolated nucleic acid comprising nucleotides 155 through 835 of the nucleic acid sequence designated SEQ. I.D. No. 1.

3. An isolated nucleic acid, comprising nucleotides 155 through 835 of SEQ ID NO:1, but with "AGA" in positions 587–589.

4. An isolated nucleic acid encoding a polypeptide having an amino acid sequence that is the same as amino acid residues 174 through 400 of the amino acid sequence designated SEQ. I.D. No. 3.

5. An isolated nucleic acid which encodes a peptide having the amino acid sequence of SEQ ID NO:3.

6. A vector comprising the isolated nucleic acid of claim 2.

7. A vector comprising the isolated nucleic acid of claim 3.

8. The vector of claim 6, wherein the vector comprises viral DNA.

9. A method of obtaining a polypeptide in purified form which comprises:
    (a) introducing the vector of claim 6 into a suitable host cell;
    (b) culturing the resulting host cell so as to produce the polypeptide;
    (c) recovering the polypeptide produced into step (b); and
    (d) purifying the polypeptide so recovered.

10. A method of obtaining a peptide in purified form which comprises:
    (a) introducing the vector of claim 7 into a suitable host cell;
    (b) culturing the resulting host cell so as to produce the polypeptide;
    (c) recovering the polypeptide produced into step (b); and
    (d) purifying the polypeptide so recovered.

\* \* \* \* \*

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 3215 base pairs
      (B) TYPE: nucleic acid
      (C) STRANDEDNESS: double
      (D) TOPOLOGY: circular (xi) SEQUENCE DESCRIPTION: SEQ ID NO: 1:

```
CTCCACCACT TTCCACCAAA CTCTTCAAGA TCCCAGAGTC AGGGCCCTGT ACTTTCCTGC        60

TGGTGGCTCC AGTTCAGGAA CAGTGAGCCC TGCTCAGAAT ACTGTCTCTG CCATATCGTC       120

AATCTTATCG AAGACTGGGG ACCCTGTACC GAACATGGAG AACATCGCAT CAGGACTCCT       180

AGGACCCCTG CTCGTGTTAC AGGCGGGGTT TTTCTTGTTG ACAAAAATCC TCACAATACC       240

GCAGAGTCTA GACTCGTGGT GGACTTCTCT CAATTTTCTA GGGGGAACAC CCGTGTGTCT       300

TGGCCAAAAT TCGCAGTCCC AAATCTCCAG TCACTCACCA ACCTGTTGTC CTCCAATTTG       360

TCCTGGTTAT CGCTGGATGT GTCTGCGGCG TTTTATCATC TTCCTCTGCA TCCTGCTGCT       420

ATGCCTCATC TTCTTGTTGG TTCTTCTGGA CTATCAAGGT ATGTTGCCCG TTTGTCCTCT       480

AATTCCAGGA TCAACAACAA CCAGCACCGG ACCATGCAAA ACCTGCACAA CTCCTGCTCA       540

AGGAACCTCT ATGTTTCCCT CATGTTGCTG TACAAAACCT ACGGACAGAA ACTGCACCTG       600

TATTCCCATC CCATCATCTT GGGCTTTCGC AAAATACCTA TGGGAGTGGG CCTCAGTCCG       660

TTTCTCTTGG CTCAGTTTAC TAGTGCCATT TGTTCAGTGG TTCGTAGGGC TTTCCCCCAC       720

TGTCTGGCTT TCAGTTATAT GGATGATGTG GTTTTGGGGG CCAAGTCTGT ACAACATCTT       780

GAGTCCCTTT ATGCCGCTGT TACCAATTTT CTTTTGTCTT TGGGTATACA TTTAAACCCT       840

CACAAAACAA AAAGATGGGG ATATTCCCTT AACTTCATGG GATATGTCAT TGGGAGTTGG       900

GGCACATTGC CACAGGAACA TATTGTACAA AAAATCAAAA TGTGTTTTAG GAAACTTCCT       960

GTAAACAGGC CTATTGATTG GAAAGTATGT CAACGAATTG TGGGTCTTTT GGGGTTTGCC      1020

GCCCCTTTCA CGCAATGTGG ATATCCTGCT TTAATGCCTT TATATGCATG TATACAAGCA      1080
```

```
                                         -continued

AAACAGGCTT TTACTTTCTC GCAAACTTAC AAGACCTTTC TAAGTAAACA GTATCTGAAC    1140

CTTTACCCCG TTGCTCGGCA ACGCCCTGGT CTGTGCCAAG TGTTTGCTGA CGCAACCCCC    1200

ACTGGTTGGG GCTTGGCCAT AGGCCATCAG CGCATGCGTG GAACCTTTGT GTCTCCTCTG    1260

CCGATCCATA CTGCGGAACT CCTAGCCGCT TGTTTTGCTC GCAGCAGGTC TGGGGCAAAA    1320

CTCATCGGGA CTGACAATTC TGTCGTGCTC TCCCGCAAGT ATACATCATT TCCATGGCTG    1380

CTAGGCTGTG CTGCCAACTG GATCCTGCGC GGGACGTCCT TTGTTTACGT CCCGTCGGCG    1440

CTGAATCCCG CGGACGACCC CTCCCGGGGC CGCTTGGGGC TCTACCGCCC GCTTCTCCGC    1500

CTGTTATACC GACCGACCAC GGGGCGCACC TCTCTTTACG CGGACTCCCC GTCTGTGCCT    1560

TCTCATCTGC CGGACCGTGT GCACTTCGCT TCACCTCTGC ACGTCGCATG GAGACCACCG    1620

TGAACGCCCA CGGGAACCTG CCCAAGGTCT TGCATAAGAG GACTCTTGGA CTTTCAGCAA    1680

TGTCAACGAC CGACCTTGAG GCATACTTCA AAGACTGTGT GTTTAATGAG TGGGAGGAGT    1740

TGGGGGAGGA GGTTAGGTTA AAGGTCTTTG TACTAGGAGG CTGTAGGCAT AAATTGGTGT    1800

GTTCACCATC ACCATGCAAC TTTTTCACCT CTGCCTAATC ATCTCATGTT CATGTCCTAC    1860

TGTTCAAGCC TCCAAGCTGT GCCTTGGGTG GCTTTGGGGC ATGGACATTG ACCCGTATAA    1920

AGAATTTGGA GCTTCTGTGG AGTTACTCTC TTTTTTGCCT TCTGACTTTT TTCCTTCTAT    1980

TCGAGATCTC CTCGACACCG CCTCTGCTCT GTATCGGGAG GCCTTAGAGT CTCCGGAACA    2040

TTGTTCACCT CACCATACGG CACTCAGGCA AGCTATTCTG AGTTGGGGTG AGTTAATGAA    2100

TCTAGCCACC TGGGTGGGAA GTAATTTGGA AGATCCAGCA TCCAGGGAAT TAGTAGTCAG    2160

CTATGTCAAC GTTAATATGG GCCTAAAAAT CAGACAACTA TTGTGGTTTC ACATTTCCTG    2220

TCTTACTTTT GGGAGAGAAA CTGTTCTTGA ATATTTGGTG TCTTTTGGAG TGTGGATTCG    2280

CACTCCTCCT GCATATAGAC CACCAAATGC CCCTATCTTA TCAACACTTC CGGAAACTAC    2340

TGTTGTTAGA CGAAGAGGCA GGTCCCCTAG AAGAAGAACT CCCTCGCCTC GCAGACGAAG    2400

GTCTCAATCG CCGCGTCGCA GAAGATCTCA ATCTCGGGAA TCTCAATGTT AGTATTCCTT    2460

GGACACATAA GGTGGGAAAC TTTACGGGGC TTTATTCTTC TACGGTACCT TGCTTTAATC    2520

CTAAATGGCA AACTCCTTCT TTTCCGGACA TTCATTTGCA GGAGGACATT CTTGATAGAT    2580

GTAAGCAATT TGTGGGGCCC CTTACAGTAA ATGAAAACAG GAGACTAAAA TTAATTATGC    2640

CTGCTAGGTT TTATCCAAAT GTTACTAAAT ATTTGCCCTT AGATAAAGGG ATCAAACCAT    2700

ATTATCCAGA GTATGTAGTT AATCATTACT TCCAGACGCG ACATTATTTA CACACTCTTT    2760

GGAAGGCGGG GATCTTATAT AAAAGAGAGT CCACACGTAG CGCCTCATTT TGCGGGTCAC    2820

CATATTCTTG GAACAAGAT CTACAGCATG GGAGGTTGGT CTTCCAAACC TCGAAAAGGC    2880

ATGGGACAA ATCTTTCTGT CCCCAATCCC CTGGGATTCT TCCCCGATCA TCAGTTGGAC    2940

CCTGCATTCA AAGCCAACTC AGAAAATCCA GATTGGGACC TCAACCCGCA CAAGGACAAC    3000

TGGCCGGACG CCAACAAGGT GGGAGTGGGA GCATTCGGGC CAGGGTTCAC CCCTCCTCAT    3060

GGGGGACTGT TGGGGTGGAG CCCTCAGGCT CAGGGCCTAC TCACAACTGT GCCAGCAGCT    3120

CCTCCTCCTG CCTCCACCAA TCGGCAGTCA GGAAGGCAGC CTACTCCCTT ATCTCCACCT    3180

CTAAGGGACA CTCATCCTCA GGCCATGCAG TGGAA                              3215

(2) INFORMATION FOR SEQ ID NO: 2:

(i) SEQUENCE CHARACTERISTICS:
        (A) LENGTH: 843 amino acids
        (B) TYPE: amino acid
```

(C) STRANDEDNESS: single
(D) TOPOLOGY: linear (xi) SEQUENCE DESCRIPTION: SEQ ID NO: 2:

```
Met Pro Leu Ser Tyr Gln His Phe Arg Lys Leu Leu Leu Asp Glu
1               5                   10                  15

Glu Ala Gly Pro Leu Glu Glu Leu Pro Arg Leu Ala Asp Glu Gly
                20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
50                  55                      60

Ser Thr Val Pro Cys Phe Asn Pro Lys Trp Gln Thr Pro Ser Phe Pro
65                  70                  75                  80

Asp Ile His Leu Gln Glu Asp Ile Leu Asp Arg Cys Lys Gln Phe Val
                85                  90                  95

Glu Pro Leu Thr Val Asn Glu Asn Arg Arg Leu Lys Leu Ile Met Pro
                100                 105                 110

Ala Arg Phe Tyr Pro Asn Val Thr Lys Tyr Leu Pro Leu Asp Lys Gly
        115                 120                 125

Ile Lys Pro Tyr Tyr Pro Glu Tyr Val Val Asn His Tyr Phe Gln Thr
130                 135                 140

Arg His Tyr Leu His Thr Leu Trp Lys Ala Gly Ile Leu Tyr Lys Arg
145                 150                 155                 160

Glu Ser Thr Arg Ser Ala Ser Phe Cys Gly Ser Pro Tyr Ser Trp Glu
                165                 170                 175

Gln Asp Leu Gln His Gly Arg Leu Val Phe Gln Thr Ser Lys Arg His
                180                 185                 190

Gly Asp Lys Ser Phe Cys Pro Glu Ser Pro Gly Ile Leu Pro Arg Ser
                195                 200                 205

Ser Val Gly Pro Cys Ile Gln Ser Gln Leu Arg Lys Ser Arg Leu Gly
                210                 215                 220

Pro Gln Pro Ala Gln Gly Gln Leu Ala Gly Arg Gln Gln Gly Gly Ser
225                 230                 235                 240

Gly Ser Ile Arg Ala Arg Val His Pro Ser Ser Trp Gly Thr Val Gly
                245                 250                 255

Val Glu Pro Ser Gly Ser Gly Pro Thr His Asn Cys Ala Ser Ser Ser
                260                 265                 270

Ser Ser Cys Leu His Gln Ser Ala Val Arg Lys Ala Ala Tyr Ser Leu
        275                 280                 285

Ile Ser Thr Ser Lys Gly His Ser Ser Ser Gly His Ala Val Glu Leu
        290                 295                 300

His His Phe Pro Pro Asn Ser Ser Arg Ser Gln Ser Gln Gly Pro Val
305                 310                 315                 320

Leu Ser Cys Trp Trp Leu Gln Phe Arg Asn Ser Glu Pro Cys Ser Glu
                325                 330                 335

Tyr Cys Leu Cys His Ile Val Asn Leu Ile Glu Asp Trp Gly Pro Cys
                340                 345                 350

Thr Glu His Gly Glu His Arg Ile Arg Thr Pro Arg Thr Pro Ala Arg
                355                 360                 365

Val Thr Gly Gly Val Phe Leu Val Asp Lys Asn Pro His Asn Thr Ala
                370                 375                 380

Glu Ser Arg Leu Val Val Asp Phe Ser Gln Phe Ser Arg Gly Asn Thr
385                 390                 395                 400
```

-continued

```
Arg Val Ser Trp Pro Lys Phe Ala Val Pro Asn Leu Gln Ser Leu Thr
                405                 410                 415
Asn Leu Leu Ser Ser Asn Leu Ser Trp Leu Ser Leu Asp Val Ser Ala
            420                 425                 430
Ala Phe Tyr His Leu Pro Leu His Pro Ala Ala Met Pro His Leu Leu
        435                 440                 445
Val Gly Ser Ser Gly Leu Ser Arg Tyr Val Ala Arg Leu Ser Ser Asn
    450                 455                 460
Ser Arg Ile Asn Asn Asn Glu His Arg Thr Met Glu Asn Leu His Asn
465                 470                 475                 480
Ser Cys Ser Arg Asn Leu Tyr Val Ser Leu Met Leu Leu Tyr Lys Thr
                485                 490                 495
Tyr Gly Gln Lys Leu His Leu Tyr Ser His Pro Ile Ile Leu Gly Phe
            500                 505                 510
Arg Lys Ile Pro Met Gly Val Gly Leu Ser Pro Phe Leu Leu Ala Gln
        515                 520                 525
Phe Thr Ser Ala Ile Cys Ser Val Val Arg Arg Ala Phe Pro His Cys
    530                 535                 540
Leu Ala Phe Ser Tyr Met Asp Asp Val Val Leu Gly Ala Lys Ser Val
545                 550                 555                 560
Gln His Leu Glu Ser Leu Tyr Ala Ala Val Thr Asn Phe Leu Leu Ser
                565                 570                 575
Leu Gly Ile His Leu Asn Pro His Lys Thr Lys Arg Trp Gly Tyr Ser
            580                 585                 590
Leu Asn Phe Met Gly Tyr Val Ile Gly Ser Trp Gly Thr Leu Pro Gln
        595                 600                 605
Glu His Ile Val Gln Lys Ile Lys Met Cys Phe Arg Lys Leu Pro Val
    610                 615                 620
Asn Arg Pro Ile Asp Trp Lys Val Cys Gln Arg Ile Val Gly Leu Leu
625                 630                 635                 640
Gly Phe Ala Ala Pro Phe Thr Gln Cys Gly Tyr Pro Ala Leu Met Pro
                645                 650                 655
Leu Tyr Ala Cys Ile Gln Ala Lys Gln Ala Phe Thr Phe Ser Gln Thr
            660                 665                 670
Tyr Lys Thr Phe Leu Ser Lys Gln Tyr Leu Asn Leu Tyr Pro Val Ala
        675                 680                 685
Arg Gln Arg Pro Gly Leu Cys Glu Val Phe Ala Asp Ala Thr Pro Thr
    690                 695                 700
Gly Trp Gly Leu Ala Ile Gly His Gln Arg Met Arg Gly Thr Phe Val
705                 710                 715                 720
Ser Pro Leu Pro Ile His Thr Ala Glu Leu Leu Ala Ala Cys Phe Ala
                725                 730                 735
Arg Ser Arg Ser Gly Ala Lys Leu Ile Gly Thr Asp Asn Ser Val Val
            740                 745                 750
Leu Ser Arg Lys Tyr Thr Ser Phe Pro Trp Leu Leu Gly Cys Ala Ala
        755                 760                 765
Asn Trp Ile Leu Arg Gly Thr Ser Phe Val Tyr Val Pro Ser Ala Leu
    770                 775                 780
Asn Pro Ala Asp Asp Pro Ser Arg Gly Arg Leu Gly Leu Tyr Arg Pro
785                 790                 795                 800
Leu Leu Arg Leu Leu Tyr Arg Pro Thr Thr Gly Arg Thr Ser Leu Tyr
                805                 810                 815
```

```
Ala Asp Ser Pro Ser Val Pro Ser His Leu Pro Asp Arg Val His Phe
            820                 825                 830

Ala Ser Pro Leu His Val Ala Trp Arg Pro Pro
            835                 840
```

(2) INFORMATION FOR SEQ ID NO: 3:

(i) SEQUENCE CHARACTERISTICS:
       (A) LENGTH: 400 amino acids
       (B) TYPE: amino acid
       (C) STRANDEDNESS: single
       (D) TOPOLOGY: linear (xi) SEQUENCE DESCRIPTION: SEQ ID NO: 3:

```
Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
            35                  40                  45

Lys Asp Asn Trp Pro Asp Ala Asn Lys Val Gly Val Gly Ala Phe Gly
50                  55                  60

Pro Gly Phe Thr Pro Pro His Gly Gly Leu Leu Gly Trp Ser Pro Gln
65                  70                  75                  80

Ala Gln Gly Leu Leu Thr Thr Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala Met Gln Trp Asn Ser Thr Thr Phe His
            115                 120                 125

Gln Thr Leu Gln Asp Pro Arg Val Arg Ala Leu Tyr Phe Pro Ala Gly
    130                 135                 140

Gly Ser Ser Ser Gly Thr Val Ser Pro Ala Gln Asn Thr Val Ser Ala
145                 150                 155                 160

Ile Ser Ser Ile Leu Ser Lys Thr Gly Asp Pro Val Pro Asn Met Glu
                165                 170                 175

Asn Ile Ala Ser Gly Leu Leu Gly Pro Leu Leu Val Leu Gln Ala Gly
            180                 185                 190

Phe Phe Leu Leu Thr Lys Ile Leu Thr Ile Pro Gln Ser Leu Asp Ser
        195                 200                 205

Trp Trp Thr Ser Leu Asn Phe Leu Gly Gly Thr Pro Val Cys Leu Gly
210                 215                 220

Gln Asn Ser Gln Ser Gln Ile Ser Ser His Ser Pro Thr Cys Cys Pro
225                 230                 235                 240

Pro Ile Cys Pro Gly Tyr Arg Trp Met Cys Leu Arg Arg Phe Ile Ile
            245                 250                 255

Phe Leu Cys Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Thr
    275                 280                 285

Thr Thr Ser Thr Gly Pro Cys Lys Thr Cys Thr Thr Pro Ala Gln Gly
290                 295                 300

Thr Ser Met Phe Pro Ser Cys Cys Cys Thr Lys Pro Thr Asp Arg Asn
305                 310                 315                 320

Cys Thr Cys Ile Pro Ile Pro Ser Ser Trp Ala Phe Ala Lys Tyr Leu
            325                 330                 335
```

```
Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
            355                 360                 365

Ile Trp Met Met Trp Phe Trp Gly Pro Ser Leu Tyr Asn Ile Leu Ser
            370                 375                 380

Pro Phe Met Pro Leu Leu Pro Ile Phe Phe Cys Leu Trp Val Tyr Ile
385                 390                 395                 400

(2) INFORMATION FOR SEQ ID NO: 4:

(i) SEQUENCE CHARACTERISTICS:
        (A) LENGTH: 212 amino acids
        (B) TYPE: amino acid
        (C) STRANDEDNESS: single
        (D) TOPOLOGY: linear (xi) SEQUENCE DESCRIPTION: SEQ ID NO: 4:

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Ser Val Glu Leu Leu Ser Phe Leu
            35                  40                  45

Pro Ser Asp Phe Phe Pro Ser Ile Arg Asp Leu Leu Asp Thr Ala Ser
50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Ser Trp Gly Glu Leu Met Asn
            85                  90                  95

Leu Ala Thr Trp Val Gly Ser Asn Leu Glu Asp Pro Ala Ser Arg Glu
            100                 105                 110

Leu Val Val Ser Tyr Val Asn Val Asn Met Gly Leu Lys Ile Arg Gln
            115                 120                 125

Leu Leu Trp Phe His Ile Ser Cys Leu Thr Phe Gly Arg Glu Thr Val
            130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
            165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Cys
    210

(2) INFORMATION FOR SEQ ID NO: 5:

(i) SEQUENCE CHARACTERISTICS:
        (A) LENGTH: 154 amino acids
        (B) TYPE: amino acid
        (C) STRANDEDNESS: single
        (D) TOPOLOGY: linear (xi) SEQUENCE DESCRIPTION: SEQ ID NO: 5:

Met Ala Ala Arg Leu Cys Cys Gln Leu Asp Pro Ala Arg Asp Val Leu
1               5                   10                  15
```

```
Cys Leu Arg Pro Val Gly Ala Glu Ser Arg Gly Arg Pro Leu Pro Gly
         20                  25                  30

Pro Leu Gly Ala Leu Pro Pro Ala Ser Pro Pro Val Ile Pro Thr Asp
             35                  40                  45

His Gly Ala His Leu Ser Leu Arg Gly Leu Pro Val Cys Ala Phe Ser
         50                  55                  60

Ser Ala Gly Pro Cys Ala Leu Arg Phe Thr Ser Ala Arg Arg Met Glu
 65                  70                  75                  80

Thr Thr Val Asn Ala His Gly Asn Leu Pro Lys Val Leu His Lys Arg
                 85                  90                  95

Thr Leu Gly Leu Ser Ala Met Ser Thr Thr Asp Leu Glu Ala Tyr Phe
             100                 105                 110

Lys Asp Cys Val Phe Asn Glu Trp Glu Leu Gly Glu Glu Val Arg
             115                 120                 125

Leu Lys Val Phe Val Leu Gly Gly Cys Arg His Lys Leu Val Cys Ser
         130                 135                 140

Pro Ser Pro Cys Asn Phe Phe Thr Ser Ala
145                 150

(2) INFORMATION FOR SEQ ID NO: 6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 6:

ATAAGCTTAT GCCCCTATCT TATCAACACT TCCGGA                              36

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 7:

GAGTCTAGAC TCTGCGGTAT TGTGA                                          25

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 8:

GAGTCTAGAC TCGTGGTGGA CTTCT                                          25

(2) INFORMATION FOR SEQ ID NO: 9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 9:

TGAGAATTCT CACGGTGGTC TCCATGCGAC GT                                  32
```

(2) INFORMATION FOR SEQ ID NO: 10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear     (xi) SEQUENCE DESCRIPTION: SEQ ID NO: 10:

TTTGTTTACG TCCCGT                                                        16

(2) INFORMATION FOR SEQ ID NO: 11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (xi) SEQUENCE DESCRIPTION: SEQ ID NO: 11:

CTAAGCTTAG TTTCCGGAAG TGTTGAT                                   27